United States Patent
Gilbert et al.

(10) Patent No.: US 10,283,120 B2
(45) Date of Patent: May 7, 2019

(54) METHOD AND APPARATUS FOR PRODUCING OUTPUT INDICATIVE OF THE CONTENT OF SPEECH OR MOUTHED SPEECH FROM MOVEMENT OF SPEECH ARTICULATORS

(71) Applicant: The University of Hull, Humberside, Hull (GB)

(72) Inventors: James Michael Gilbert, Hull (GB); Lam Aun Cheah, Hull (GB); Jie Bai, Hull (GB)

(73) Assignee: The University of Hull, Hull (GB)

(*) Notice: Subject to any disclaimer, the term of this patent is extended or adjusted under 35 U.S.C. 154(b) by 71 days.

(21) Appl. No.: 15/511,923

(22) PCT Filed: Sep. 15, 2015

(86) PCT No.: PCT/EP2015/071042
§ 371 (c)(1),
(2) Date: Mar. 16, 2017

(87) PCT Pub. No.: WO2016/041934
PCT Pub. Date: Mar. 24, 2016

(65) Prior Publication Data
US 2017/0249942 A1     Aug. 31, 2017

(30) Foreign Application Priority Data
Sep. 16, 2014 (GB) .................................. 1416311.7

(51) Int. Cl.
*G10L 15/24* (2013.01)
*G10L 15/25* (2013.01)
(Continued)

(52) U.S. Cl.
CPC ................ *G10L 15/25* (2013.01); *A61B 5/05* (2013.01); *A61B 5/1114* (2013.01); *A61B 5/682* (2013.01);
(Continued)

(58) Field of Classification Search
CPC ........... G10L 15/24; G10L 13/04; A61B 5/05; A61B 5/1114; A61B 5/682
(Continued)

(56) References Cited

U.S. PATENT DOCUMENTS

| 5,594,469 A * | 1/1997 | Freeman | ............. G05B 19/106 345/157 |
| 5,670,987 A * | 9/1997 | Doi | ........................ B25J 9/1692 345/156 |

(Continued)

FOREIGN PATENT DOCUMENTS

| GB | 2378776 A | 2/2003 |
| GB | 2422238 A | 7/2006 |

(Continued)

OTHER PUBLICATIONS

Gilbert et al. "Isolated word recognition of silent speech using magnetic implants and sensors" Medical engineering & physics 32.10 (2010): 1189-1197.*

(Continued)

*Primary Examiner* — Seong-Ah A Shin
(74) *Attorney, Agent, or Firm* — Maschoff Brennan

(57) ABSTRACT

A method of producing output indicative of the content of speech or mouthed speech from movement of speech articulators is described. The method may including fixing a plurality of magnets respectively to a plurality of speech articulators of a human individual. Providing a support. Providing a plurality of signal magnetic field sensors. Providing at least three reference magnetic field sensors orien- (Continued)

tated differently from one another with respect to the Earth's magnetic field. The signal and reference magnetic field sensors being fixed to the support which holds the sensors in fixed spatial relationships to one another. Producing, over a period of time, a respective signal from each signal magnetic field sensor and a respective signal from each reference magnetic field sensor. Obtaining, over the period of time, for each said signal magnetic field sensor signal, a respective correction value.

18 Claims, 4 Drawing Sheets

(51) Int. Cl.
| | | |
|---|---|---|
| *A61B 5/00* | (2006.01) | |
| *G10L 13/04* | (2013.01) | |
| *A61B 5/05* | (2006.01) | |
| *A61B 5/11* | (2006.01) | |
| *G01R 33/02* | (2006.01) | |

(52) U.S. Cl.
CPC .............. *G10L 13/04* (2013.01); *G10L 15/24* (2013.01); *A61B 5/741* (2013.01); *A61B 2562/0223* (2013.01); *G01R 33/0206* (2013.01)

(58) Field of Classification Search
USPC .................................. 704/261, 243, 255, 275
See application file for complete search history.

(56) References Cited

U.S. PATENT DOCUMENTS

| | | | | |
|---|---|---|---|---|
| 6,002,808 | A * | 12/1999 | Freeman .................. | G06F 3/017 |
| | | | | 348/171 |
| 6,147,678 | A * | 11/2000 | Kumar .................... | G06F 3/017 |
| | | | | 345/156 |
| 6,256,400 | B1 | 7/2001 | Takata | |
| 6,343,269 | B1 * | 1/2002 | Harada .................... | G10L 15/24 |
| | | | | 704/243 |
| 6,532,447 | B1 * | 3/2003 | Christensson ........ | H04M 1/271 |
| | | | | 704/275 |
| 7,333,089 | B1 * | 2/2008 | Gard ....................... | G06F 3/011 |
| | | | | 345/157 |
| 2002/0126876 | A1 | 9/2002 | Paul | |
| 2002/0181773 | A1 | 12/2002 | Higaki | |
| 2007/0121065 | A1 * | 5/2007 | Cox ....................... | A61B 3/113 |
| | | | | 351/209 |
| 2009/0153366 | A1 * | 6/2009 | Im .......................... | G06F 3/017 |
| | | | | 341/20 |
| 2016/0027441 | A1 * | 1/2016 | Liu .......................... | G10L 15/25 |
| | | | | 704/255 |
| 2016/0378195 | A1 * | 12/2016 | Lefebvre ................ | G06F 3/017 |
| | | | | 382/156 |
| 2017/0263237 | A1 * | 9/2017 | Green ..................... | G10L 13/04 |

FOREIGN PATENT DOCUMENTS

| | | |
|---|---|---|
| JP | H06142084 A | 5/1994 |
| JP | H07248873 A | 9/1995 |
| JP | H09179988 A | 7/1997 |
| JP | 2001246161 A | 9/2001 |
| WO | 2006075179 A1 | 7/2006 |
| WO | 2006102495 A2 | 9/2006 |

OTHER PUBLICATIONS

Hofe et al. "Small-vocabulary speech recognition using a silent speech interface based on magnetic sensing." Speech Communication 55.1 (2013): 22-32.*

Gilbert et al. "Isolated word recognition of silent speech using magnetic implants and sensors" Medical engineering & physics 32.10 (2010): 1189-1197 (Year: 2010).*

Hofe et al. "Small-vocabulary speech recognition using a silent speech interface based on magnetic sensing." Speech Communication 55.1 (2013): 22-32 (Year: 2013).*

Gilbert et al., "Isolated word recognition of silent speech using magnetic implants and sensors", Medical Engineering & Physics, Butterworth-Heinmann, GB, vol. 32, No. 10, Dec. 1, 2010, pp. 1189-1197.

Hofe et al., "Small-vocabulary speech recognition using a silent speech interface based on magnetic sensing", Speech Communication, vol. 55, No. 1, Feb. 12, 2012, pp. 22-32.

Gonzalez et al., "Analysis of Phonetic Similarity in a Silent Speech Interface based on Permanent Magnetic Articulography", Interspeech 2014: 15th Annual Conference of the International Speech Communication Association, Sep. 16, 2014, pp. 1018-1022.

Sonoda, Y., "Observation of tongue movements employing magnetometer sensor", Magnetics IEEE Transactions on 10.3 (1974), pp. 954-957.

Fagan, M. J. et al., "Development of a (silent) speech recognition system for patients following laryngectomy", Medical Engineering & Physics 30 (2008), pp. 419-425.

Denby, B. et al., "Silent speech interfaces", Speech Communication 52 (2010), pp. 270-287.

Cheah, L. A. et al., "Integrating user-centred design in the development of a silent speech interface based on permanent magnetic articulography", in: Biomedical engineering systems and technologies 8th international joint conference, BIOSTEC 2015, Lisbon, Portugal, Jan. 12-15, 2015, Revised Selected Papers, Communications in Computer and Information Science (CCIS).

European Search Report dated Mar. 11, 2015 for Application No. GB1416311.7.

* cited by examiner

METHOD AND APPARATUS FOR PRODUCING OUTPUT INDICATIVE OF THE CONTENT OF SPEECH OR MOUTHED SPEECH FROM MOVEMENT OF SPEECH ARTICULATORS

The invention relates to a method and an apparatus for producing output indicative of the content of speech or mouthed speech from movement of speech articulators.

Mouthed speech refers to a person moving his or her mouth as if that person was speaking, but without any sound being made, or with only a very quiet sound being made.

A speech articulator is a part of the human mouth that is involved in the production of normal speech. For example, the articulators include the upper and lower lips, the tip of the tongue, the mid-point (or hump) of the tongue, the upper and lower teeth, the alveolar ridge, the velum (soft palate), the uvula and the hard palate. Some articulators move (relative to the head) during speech, such as the tongue, the lips and the lower teeth. Other articulators, such as the upper teeth, do not move. For the current purposes, a particular organ of the mouth may be considered to comprise of a plurality of articulators. For example, the left and right hand sides of the upper lip may be considered to be two separate articulators. Different parts of the tongue may be considered to be separate articulators. In general, for the current purposes, each part of the mouth to which a magnet is attached (as discussed below) will be considered to be a separate articulator.

Output, generally but not exclusively in the form of electrical signals, that is indicative of the content of speech or mouthed speech can be put to many uses. For example, some people lose the ability to make audible speech, such as patients who have undergone a laryngectomy. For such people, output that is indicative of the content of and made during mouthed speech can be used to generate artificial audible speech. Even for people who are able to speak normally, output indicative of the content of speech can be useful. For example, in very noisy environments where normal audible speech could not be heard, output indicative of the content of speech can be used for communication or for controlling machinery. Alternatively, output indicative of the content of mouthed speech may be used for communication in situations where audible speech is unacceptable, such as in covert situations for which silence is required.

WO2006/075179 A1 discloses a method of producing output indicative of the content of speech or mouthed speech from movement of speech articulators. The method comprises fixing a plurality of magnets, respectively, to a plurality of speech articulators of a human individual. A plurality of magnetic field sensors is provided. Each magnetic field sensor is located so as to be able to sense a respective magnetic field intensity comprising a component produced by at least one of the magnets. The output in WO2006/075179 A1 takes the form of the electrical signals from the magnetic field sensors. The sensors may be fixed on a support which holds the sensors in fixed spatial relationships to one another. However, the magnetic field intensities sensed by the sensors also comprise components produced by the Earth's magnetic field. These latter "noise" components can be much greater than the components produced by the magnets. In other words, there is a very low signal to noise ratio. This makes it difficult to obtain useful information from the output.

According to a first aspect of the invention, there is provided a method of producing output indicative of the content of speech or mouthed speech from movement of speech articulators, comprising: fixing a plurality of magnets respectively to a plurality of speech articulators of a human individual; providing a support; providing a plurality of signal magnetic field sensors, each said signal magnetic field sensor being located so as to be able to sense a respective magnetic field intensity comprising a component produced by at least one of the magnets and a component produced by the Earth's magnetic field; providing at least three reference magnetic field sensors orientated differently from one another with respect to the Earth's magnetic field, each said reference magnetic field sensor being located so as to be able to sense a respective magnetic field intensity produced at least partially by the Earth's magnetic field; the signal and reference magnetic field sensors being fixed to the support which holds the sensors in fixed spatial relationships to one another; producing, over a period of time, a respective signal from each signal magnetic field sensor and a respective signal from each reference magnetic field sensor, each signal being indicative of a respective magnetic field intensity sensed by the corresponding magnetic field sensor, wherein over said period of time the signals from the signal and reference magnetic field sensors change in response to movement of the support relative to the Earth's magnetic field, and the signals from the signal magnetic field sensors, and optionally also the signals from the reference magnetic field sensors, change in response to movement of the articulators; and obtaining, over said period of time, for each said signal magnetic field sensor signal, a respective correction value, each correction value being calculated using the signals from the at least three reference magnetic field sensors, each correction value being indicative of the component that is produced by the Earth's magnetic field in the magnetic field intensity sensed by the corresponding signal magnetic field sensor and each correction value changing over said time period as the component that is produced by the Earth's magnetic field in the magnetic field intensity sensed by the corresponding signal magnetic field sensor changes as the support moves.

According to a second aspect of the invention, there is provided a system for producing output indicative of the content of speech or mouthed speech from movement of speech articulators, comprising: a plurality of magnets fixable respectively to a plurality of speech articulators of a human individual; a plurality of signal magnetic field sensors for sensing respective magnetic field intensities; at least three reference magnetic field sensors for sensing respective magnetic field intensities; a support to which the signal and reference magnetic field sensors are fixed and which holds the sensors in fixed spatial relationships to one another; and processing means programmed to perform the method of the first aspect of the invention.

The correction values can be used to correct the signals from the signal magnetic field sensors produced over said period of time to give corrected output signals in which the component from the Earth's magnetic field is reduced or eliminated. Preferably, in the corrected output signals, variation is predominantly caused by movement of the articulators.

The following is a more detailed description of embodiments of the invention, by way of example, with reference being made to the appended schematic drawings in which:

FIGS. 1 to 5 show components of a system for producing output indicative of the content of speech or mouthed speech from movement of speech articulators.

Figure 1:
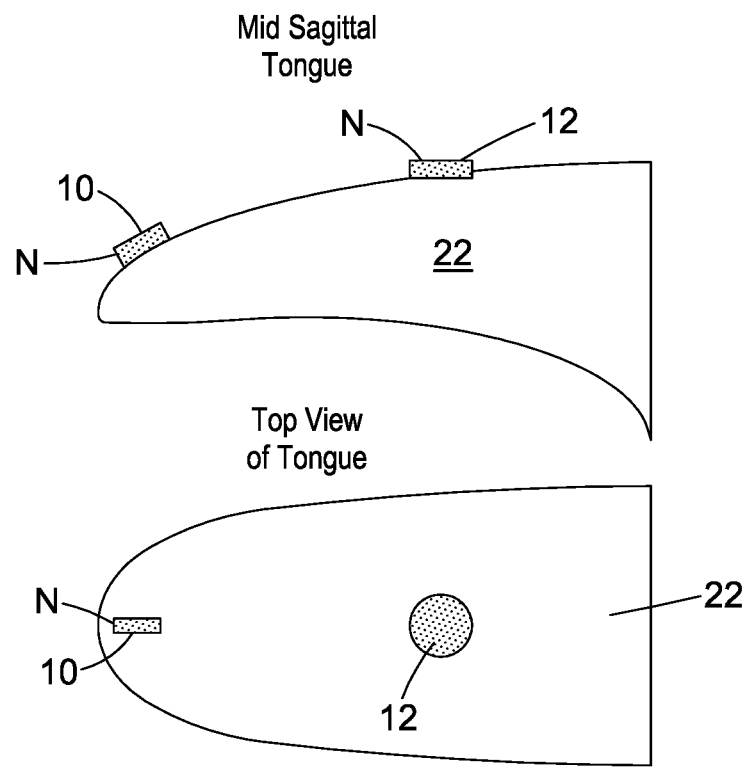
FIG. 1 shows magnets attached to the tongue of a human individual.
Figure 2:
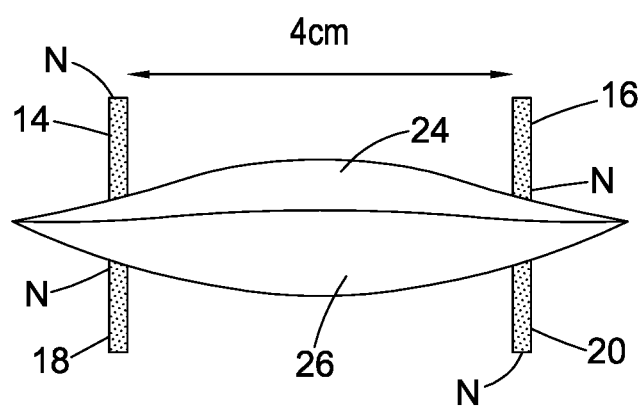
FIG. 2 shows magnets attached to the lips of the human individual.

As shown in FIGS. 1 and 2, two permanent magnets 10, 12 are fixed to the tongue 22 of a human individual, two permanent magnets 14, 16 are fixed to the upper lip 24 and two permanent magnets 18, 20 are fixed to the lower lip 26.

The magnets 10-20 are preferably Neodymium Iron Boron magnets which are high strength magnets. For long-term use, the magnets 10-20 are preferably fixed to the tongue and lips by surgical implantation. For short-term use, the magnets 10, 12 may be fixed to the tongue 22 using a suitable medical adhesive (such as Hystoacryl™ adhesive). The magnets 14-20 may be fixed to the lips 24, 26 for short-term use using medical grade self-adhesive tape.

Referring now to FIGS. 1 and 2 and to the magnets 10-20 in more detail, a first one 10 of the magnets is fixed to the tip of the tongue 22. The first magnet 10 has a diameter of 2 mm and a length of 5 mm. The North pole of the first magnet 10 faces generally forward and this is represented in FIG. 1 by the letter "N". A second one 12 of the magnets is fixed to the mid-point of the tongue 22. The second magnet 12 has a diameter of 5 mm and a length of 1 mm. The North pole of the second magnet 12 faces upward, as represented by the letter "N".

A third one 14 of the magnets is fixed to the left side of the upper lip 24 and a fourth one 16 of the magnets is fixed to the right side of the upper lip 24. The North pole of the third magnet 14 faces upwards and the North pole of the fourth magnet 16 faces downwards. The third and fourth magnets 14, 16 are separated by about 40 mm. A fifth one 18 of the magnets is fixed to the left side of the lower lip 26 and a sixth one 20 of the magnets is fixed to the right side of the lower lip 26. The fifth and sixth magnets 18, 20 are also separated by about 40 mm. The North pole of the fifth magnet 18 faces upwards and the North pole of the sixth magnet 20 faces downwards.

The third, fourth, fifth and sixth magnets 14 to 20 each have a diameter of 1 mm and a length of 5 mm.

Figure 3:
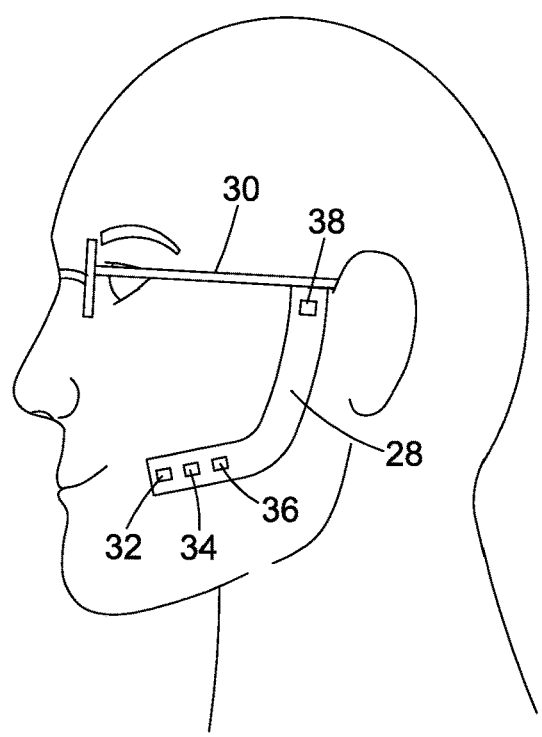
FIG. 3 is a side view of the human individual showing a support, three signal magnetic field sensor units and a reference magnetic field sensor unit.
Figure 4:
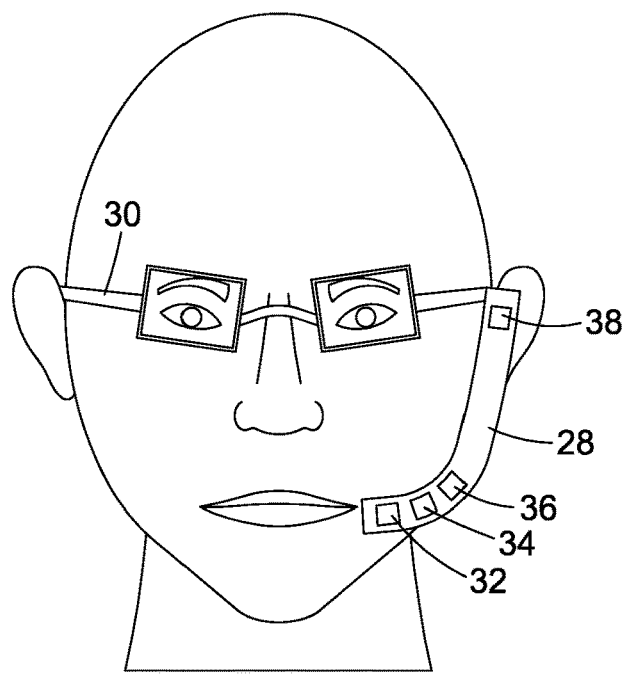
FIG. 4 is a front view of the human individual showing the support and the magnetic field sensor units of FIG. 3.

FIGS. 3 and 4 show a support 28 worn on the head of the individual to whom the magnets 10-20 have been fixed. In this embodiment, the support 28 is connected to an arm of a pair of glasses or spectacles 30 so that the support moves as the individual moves his or her head. However, the support may be worn on the individual's head in any convenient manner that causes the support 28 to move with the individual's head.

First, second and third signal magnetic field sensor units 32, 34, 36 are fixedly mounted at one end of the support 28. The shape, size and position of the support 28, and the positions of the signal magnetic field sensor units 32, 34, 36 on the support 28 are such that the signal magnetic field sensor units 32, 34, 36 are located generally adjacent to and to the side of the individual's mouth. Preferably, as best seen in FIG. 3, the signal magnetic field sensor units 32, 34, 36 are positioned generally along a straight line path aligned generally with a line extending from the opening of the individual's mouth to the back of the mouth.

Each one of the signal magnetic field sensor units 32, 34, 36 is a tri-axial sensor unit. That is to say that each signal magnetic field sensor unit 32, 34, 36 comprises, respectively, three signal magnetic field sensors which are arranged to sense, respectively, magnetic field intensity in three mutually orthogonal axes designated x, y and z. Hence, for example, the second signal magnetic field sensor unit 34 comprises three sensors, each of which senses magnetic field intensity in a respective one of three mutually orthogonal axes x, y and z. Thus, there are a total of nine signal magnetic field sensors. These are: the x, y and z sensors of the first signal magnetic field sensor unit 32; the x, y and z sensors of the second signal magnetic field sensor unit 34; and the x, y and z sensors of the third signal magnetic field sensor unit 36. As explained below, precise alignment of the sensors is not necessary. However, the three x axes may be aligned approximately parallel with one another, the three y axes may be aligned approximately parallel with one another and the three z axes may be aligned approximately parallel with one another.

The support is also provided with a reference magnetic field sensor unit 38. The reference magnetic field sensor unit 38 also comprises three sensors, each of which senses magnetic field intensity in a respective one of three mutually orthogonal axes x, y and z. Again precise alignment between the reference magnetic field sensor unit 38 and the three signal magnetic field sensor units 32-36 is not necessary. However, the x axis of the reference magnetic field sensor unit 38 may be aligned approximately parallel with the x axes of the signal magnetic field sensor units 32-36, the y axis of the reference magnetic field sensor unit 38 may be aligned approximately parallel with the y axes of the signal magnetic field sensor units 32-36, and the z axis of the reference magnetic field sensor unit 38 may be aligned approximately parallel with the z axes of the signal magnetic field sensor units 32-36.

The reference magnetic field sensor unit 38 is identical to each of the three signal magnetic field sensor units 32-36. However, as seen in FIGS. 3 and 4, the reference magnetic field sensor unit 38 is further away from the magnets 10-20 as compared to the three signal magnetic field sensor units 32-36. Indeed, the reference magnetic field sensor unit 38 is distanced sufficiently far from the magnets 10-20 so that the three magnetic field intensities (in the three axes x, y and z) sensed by the reference magnetic field sensor unit 38 do not include any substantial contribution from the magnets 10-20. In addition, the signals from the reference magnetic field sensor unit 38 are processed differently as compared to the signals from the three signal magnetic field sensor units 32-36.

Figure 5:
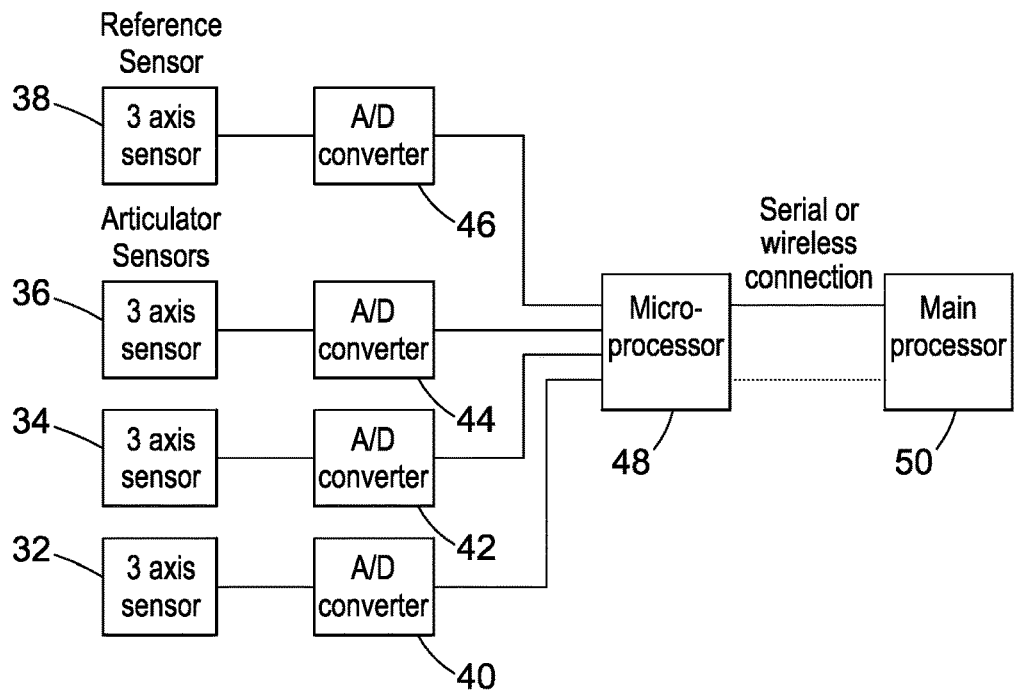
FIG. 5 shows the electronics used to process signals from the magnetic field sensor units of FIGS. 3 and 4.

FIG. 5 shows the electronics used to process the signals from the three signal magnetic field sensor units 32-36 and from the reference magnetic field sensor unit 38. Each sensor unit (signal or reference) 32-38 is connected to a respective one of four analogue-to-digital converters 40-46. Each analogue-to-digital converter 40-46 has three channels, with each channel converting the signal from a respective one of the signal or reference magnetic field sensors (x, y or z) to which the converter 40-46 is connected. The outputs from the analogue-to-digital converters 40-46 are fed into a micro-processor 48. The micro-processor 48 serves to sample the digital signals from the analogue-to-digital converters 40-46. In addition, the micro-processor 48 transmits the sampled digital signals to a main processor 50, by wireless or serial connection, for processing by the main processor 50 of the digital signals. The micro-processor 48 may also serve to supply power to the sensor units 32-38 and to the analogue-to-digital converters 40-46. The analogue-to-digital converters 40-46 and the micro-processor 48 are housed in the support 28. The main processor 50 is physically separate from the support and may be, for example, a more powerful, but portable, processor carried by the individual.

The operation of the system described above, to provide output indicative of the content of speech or mouthed speech, will now be described.

The signal magnetic field sensor units 32-36 are sufficiently close to the magnets 10-20 so that the respective magnetic field intensity sensed by each one of the nine signal magnetic field sensors (that is to say the x, y and z sensors of the first signal magnetic field sensor unit 32; the x, y and z sensors of the second signal magnetic field sensor unit 34; and the x, y and z sensors of the third signal magnetic field sensor unit 36) includes a substantial component derived from the magnets 10-20. The sensors cannot distinguish magnetic field intensity from individual magnets. Instead the component derived from the magnets 10-20 is a composite of the magnetic fields of the magnets 10-20 at the position and orientation of the sensor in question. The magnetic field intensity component sensed by each sensor, and derived from the magnets, is a composite of the magnetic fields of all six of the magnets 10-20. Alternatively, some of the signal magnetic field sensors may be influenced by some (i.e. the closer ones) but not all of the magnets 10-20.

In addition, the total magnetic field intensity sensed by each signal magnetic field sensor includes a respective component arising from the Earth's magnetic field. The component arising from the Earth's magnetic field is normally greater that the component arising from the magnets 10-20, often as much as about ten times greater. Because each one of the nine signal magnetic field sensors is orientated differently in the Earth's magnetic field, the respective component attributable to the Earth's magnetic field, in the magnetic field intensity sensed by that sensor, will be different to the components experienced by the other sensors.

As the individual talks or makes mouthed speech, the magnets 10-20 in the individual's tongue 22 and lips 24, 26 move and the patterns of movement of the magnets 10-20 vary depending on the words or sounds that are being spoken or mouthed. This is because different articulators move in different ways to produce different sounds.

Hence, the respective magnetic field intensities sensed by the nine signal magnetic field sensors vary as the individual speaks, or mouths speech, and the patterns of variation are indicative or representative of the words or sounds being spoken or mouthed. It will be noted that each one of the nine signal magnetic field sensors will experience a different pattern of variation in the component of the total magnetic field intensity that is attributable to the magnets 10-20. This is due to the fact that each sensor has a unique combination of position and orientation relative to the magnets 10-20. Different sensors will be influenced to different extents by different ones of the magnets 10-20, dependent on the position and orientation of the sensor.

A potential problem, however, is that if the individual moves his or her head while speaking, the signal magnetic field sensor units 32-36 will undergo changes in orientation relative to the Earth's magnetic field and this causes large changes in the respective magnetic field intensities sensed by the nine signal magnetic field sensors.

Figure 7:
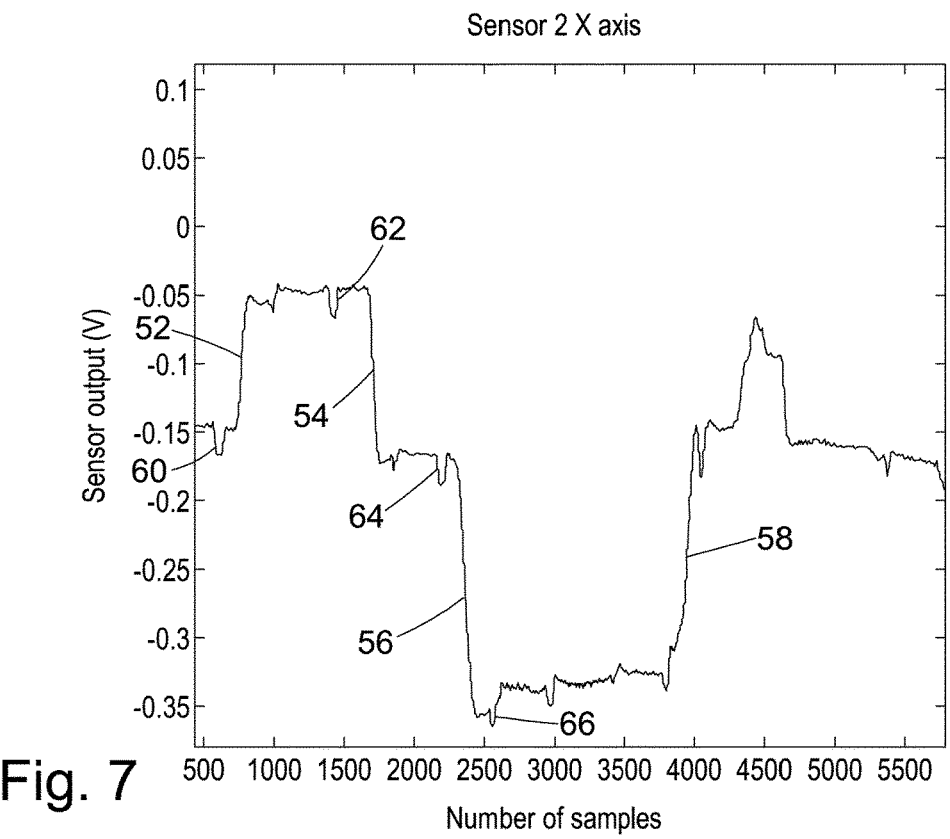
FIG. 7 is a graph showing an uncorrected signal from one of the signal magnetic field sensors of FIGS. 3 and 4.

FIG. 7 demonstrates the effect of movement of the individual's head. FIG. 7 shows a signal that is produced by the x axis sensor of the second signal magnetic field sensing unit 34. The signal is indicative of the magnetic field intensity experienced by the sensor over time as the individual moves his or her head and speaks. The large changes in intensity indicated in FIG. 7 at 52, 54, 56 and 58 are caused by head movement. In contrast, the changes in intensity caused by movement of the magnets 10-20 during speech are much smaller. Some of the changes in intensity caused by movement of the magnets during speech are indicated in FIG. 7 at 60, 62, 64, and 66. Of course, eight other signals are produced simultaneously from the eight other signal magnetic field sensors. All nine signals differ from one another.

Changes in the signals caused by movement of the head are not, of course, indicative of the content of speech or mouthed speech and it is desirable to remove them so as to isolate the signal that is caused by movement of the magnets 10-20. The manner in which this is achieved is described below.

The processing to remove the changes caused by head movement is carried out in the main processor 50 after the raw signals from the signal and reference magnetic field sensor units 32-36 and 38 have passed though the analogue-to-digital converters 40-46 and the micro-processor 48 as discussed above.

In essence, the processing comprises, individually for each one of the nine signal magnetic field sensors, estimating the component attributable to the Earth's magnetic field of the total magnetic field intensity that is experienced by the sensor. This estimated component may then be subtracted from the signal from the sensor and the remaining component is attributable substantially only to the magnets 10-20. The estimated component attributable to the Earth's magnetic field changes over time as the individual moves his or her head. Accordingly, the estimate needs to be produced and subtracted on a near real-time basis.

In order to produce the estimate of the component, attributable to the Earth's magnetic field, of the total magnetic field intensity that is experienced by any one of the signal magnetic field sensors, the processor 50 makes use of the three signals from the reference magnetic field sensor unit 38. For example, in order to estimate the component, attributable to the Earth's magnetic field, for the z sensor of the third signal magnetic field sensor unit 36, the processor will make use of the three signals from the three sensors (x, y and z) of the reference magnetic field sensor unit 38.

In theory, it would be possible to produce the signal and reference sensor units 32 to 38, and the support 28, with such a high degree of precision so that the support would hold the sensor units in near perfect alignment. Thus, for example, the z sensor of the third signal magnetic field sensor unit 36 would be near perfectly aligned with the z sensor of the reference magnetic field sensor unit 38. In this hypothetical case, which is not in accordance with the invention, the signal and reference z sensors would have a near identical alignment in the Earth's magnetic field and a simple subtraction of the signal from the reference sensor from the signal from the signal sensor would give a very close approximation to a magnetic field component attributable solely to the magnets 10-20. This is because the reference sensor is sufficiently far from the magnets 10-20 so that it does not sense any substantial magnetic field component from the magnets 10-20. In practice, however, the required degree of precision would be prohibitively expensive, and/or would require an unacceptably bulky support to give the necessary rigidity. In addition, the precise alignment might be lost on expansion due to changes in temperature, or as a result of accidental impact to the support.

As discussed above the first, second and third signal magnetic field sensor units 32-36 and the reference magnetic field sensor unit 38 are only approximately aligned. In view of this, in order to estimate the component, attributable to the Earth's magnetic field, of the total magnetic field intensity that is sensed by a single signal sensor, it is necessary to have a spatial transformation relating the orientations of the three reference magnetic field sensors (i.e. the x, y and z sensors of the reference sensor unit 38) to the orientation of the signal sensor in question. The orientations are with respect to the Earth's magnetic field. For example, a particular spatial transformation may relate the orientations of the x, y and z sensors of the reference magnetic field sensor unit 38 to the orientation of the z sensor of the third signal magnetic field sensor unit 36. This spatial transformation is used to estimate the Earth's magnetic field as experienced at the signal sensor, from the Earth's magnetic field sensed at each of the three reference sensors (i.e. x, y and z).

The required spatial transformations could be obtained by measuring the relative positions of the sensors mechanically. It is difficult, however, to achieve the required precision and the measurements would need to be repeated if there was any change in the relative positions of the sensors.

The preferred method to obtain each required spatial transformation is to estimate the transformation by comparing the signal from a signal sensor with the signals from the three reference magnetic field sensors. This should be done over a period of time during which the magnetic field intensities sensed by the sensors under comparison undergo no change attributable to movement of the magnets 10-20 attached to the articulators, but do undergo change attributable to movement of the sensors in the Earth's magnetic field. The easiest way to do this is to remove the support 28 bearing the sensor units 32-38 from the head of the individual so that the magnets 10-20 are out of range of the sensor units 32-38 and then to move the support 28 relative to the Earth's magnetic field. Alternatively, however, it may be done while the support 28 is worn on the individual's head by moving the individual's head while being careful not to move any articulator.

It will be appreciated that nine spatial transformations are required in total—one for each signal magnetic field sensor. Thus, the orientation of the x axis sensor of the first signal magnetic field sensor unit 32 will be related by a spatial transformation to the respective orientations of the three x, y and z sensors of the reference signal magnetic field sensor unit 38. The orientation of they axis sensor of the first signal magnetic field sensor unit 32 will be related by another spatial transformation to the respective orientations of the three x, y and z sensors of the reference signal magnetic field sensor unit 38. The orientation of the z axis sensor of the first signal magnetic field sensor unit 32 will be related by yet another spatial transformation to the respective orientations of the three x, y and z sensors of the reference signal magnetic field sensor unit 38. The same will apply to the second and third signal magnetic field sensor units 34, 36, each being related by three spatial transformations to the reference signal magnetic field sensor unit 38.

The estimation of the spatial transformations is performed as a separate procedure, before the procedure which involves estimating, for each signal magnetic field sensor, the respective component attributable to the Earth's magnetic field and subtracting these components from the signals from the signal sensors.

Figure 6:
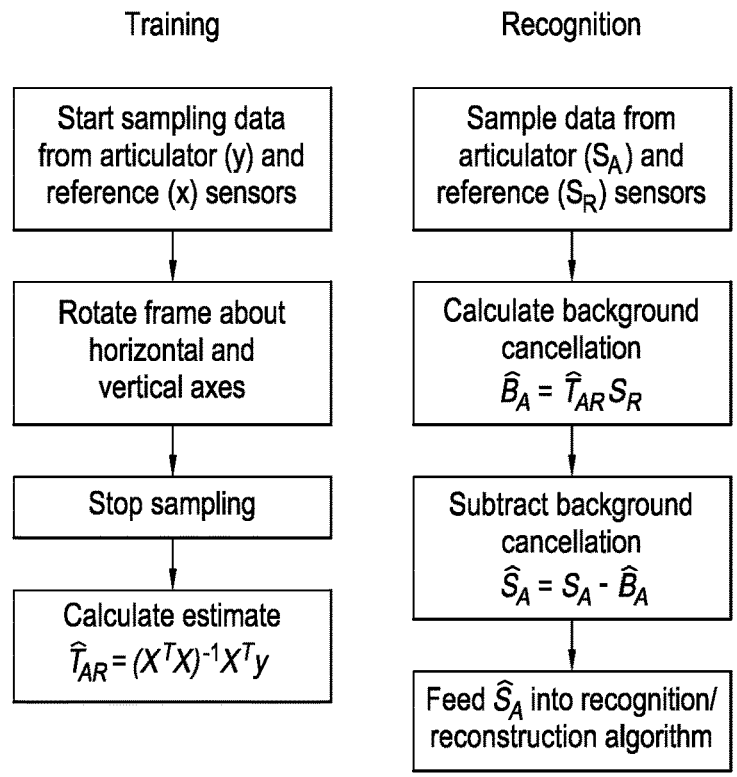
FIG. 6 is a schematic overview of a method for producing a corrected output signal in which an estimate of a component corresponding to the Earth's magnetic field is subtracted from a signal produced by one of the signal magnetic field sensor units of FIGS. 3 and 4.

The two procedures are shown schematically in FIG. 6. The left hand side of FIG. 6 is a schematic representation of the procedure for generating the spatial transformations. The right hand side of FIG. 6 is a schematic representation of the procedure for correcting for the component corresponding to the Earth's magnetic field. The estimation of the spatial transformations can be performed as and when required, for example if it is suspected that any change in relative positions of the sensors has occurred.

In FIG. 6, and in the more detailed mathematical discussion given below, the following symbols have the following meanings:

A: Signal component attributable to movement of the magnets/articulators $B_E$: Vector of the components (x, y and z) of the Earth's magnetic field $T_A$: Transformation (3×3 matrix) between Earth's magnetic field and signal sensor $T_R$: Transformation (3×3 matrix) between Earth's magnetic field and reference sensor $T_{RA}$: Transformation (3×3 matrix) between the three reference sensors and the signal sensor $S_A$: Output of a single signal sensor $S_R$: Vector containing three outputs (x, y and z) respectively of the three reference sensors $\hat{S}_A$: Output of a single signal sensor after cancellation of signal component attributable to Earth's magnetic field $B_A$: Vector containing the components of the Earth's magnetic field as experienced by a signal sensor $\hat{B}_A$: Estimate of Earth's magnetic field as experienced by a signal sensor The following is a more detailed explanation of the mathematics underlying the procedures of the current method.

As discussed above, in this embodiment, the reference magnetic field sensor unit 38 is sufficiently distant from the articulator magnets 10-20 so that it does not pick up any significant signal from them and is only affected by the background (i.e. the Earth's) magnetic field.

The signal detected by any one of the signal magnetic field sensors, $S_A$, is made up of two components: A, which represents the articulator/magnet movement; and $B_A$, which represents the background (Earth's) field sensed by the signal sensor. $B_A$ depends on the background field $B_E$ and $T_A$ which is the transformation between the Earth's coordinates and the coordinates of the signal sensor which varies due to head movement. Hence, $$S_A = A + B_A = A + B_E T_A \quad (1)$$

For any one of the reference sensors, the signal only depends on the background (Earth's) field $B_E$ and $T_R$, which is the transformation between the Earth's coordinates and the coordinates of the reference sensor so:

$$S_R = B_E T_R \quad (2)$$

If we knew the spatial transformation $T_{RA}$ between the three reference sensors and the signal sensor, then we could remove the background signal from the signal sensor signal by calculating an estimated background field $\hat{B}_A$ for the signal sensor:

$$\hat{B}_A = B_E T_R T_{RA} = S_R T_{RA} \quad (3)$$

And we could subtract this from the signal sensor signal to give:

$$\hat{S}_A = S_A - \hat{B}_A = A + B_A - \hat{B}_A$$

And provided the estimate is good ($B_A \approx \hat{B}_A$) then the effect of the background field is removed and $\hat{S}_A = A$. Unfortunately we do not know the transformation $T_{RA}$ and it may change if the frame is distorted. However, we can estimate the transformation using the least squares method if we take a series of measurements of $S_A$ and $S_R$ while rotating the sensor frame in the background field but in the absence of any articulator/magnet movement (A=0).

In the absence of articulator/magnet movement, the signal sensor signal is:

$$S_A = B_A = B_E T_A$$

While the reference sensor signal is $$S_R = B_E T_R$$

So $$B_E = S_R T_R^{-1}$$

And $$S_A = S_R T_R^{-1} T_A = S_R T_{RA}$$

Estimating $T_{RA}$ from a set of measurements of $S_A$ and $S_R$ can be accomplished using the least squares method where, if we have a model $y = X\beta + \varepsilon$ and a set of measurements of y and X, the best estimate of $\beta$ is $\hat{\beta} = (X^T X)^{-1} X^T y$. In our case, we find the least squares estimate $\hat{T}_{RA}$ and use this to estimate the effect of the background field on the signal sensor signal:

$$\hat{B}_A = S_R \hat{T}_{RA}$$

And derive a new signal sensor signal $$\hat{S}_A = S_A - \hat{B}_A = A + B_A - \hat{B}_A \quad (4)$$

or $$\hat{S}_A = A + B_E T_A - B_E T_R \hat{T}_{RA}$$

The product $T_R \hat{T}_{RA}$ may be written as $T_R \hat{T}_{RA} = \hat{T}_A$ and so:

$$\hat{S}_A = A + B_E (T_A - \hat{T}_A)$$

And if $\hat{T}_A$ provides a good estimate ($T_A \approx \hat{T}_A$) then $$\hat{S}_A \approx A \quad (5)$$

Hence, individually, for each signal magnetic field sensor, a respective corrected output signal $\hat{S}_A$ is produced in which an estimate of the component attributable to the Earth's magnetic field (a correction value) has been subtracted to leave a component attributable substantially only to the magnets 10-20.

Figure 8:
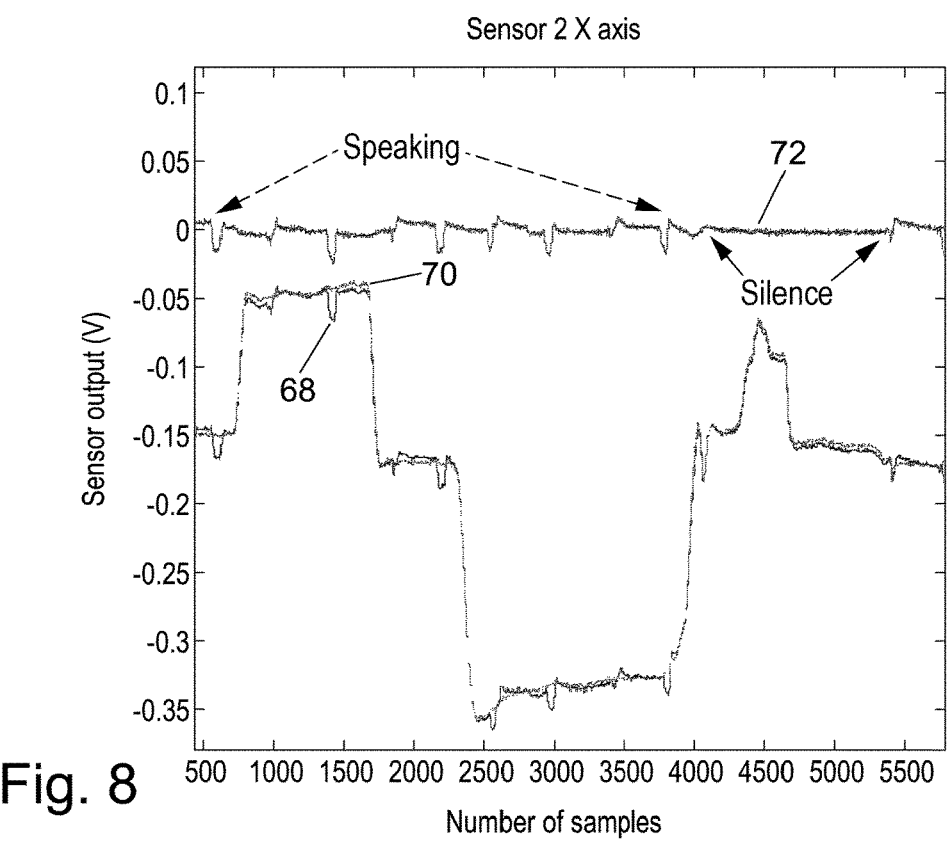
FIG. 8 is a graph of the same uncorrected signal shown in FIG. 7 and showing a corrected output signal after subtraction of a correction value.

A corrected output signal is shown in FIG. 8. In FIG. 8, trace 68 is the uncorrected signal ($S_A$) from the x axis sensor of the second signal magnetic field sensor unit 34. Trace 70 is the correction value—that is to say the estimate of the component attributable to the Earth's magnetic field ($\hat{B}_A$). Trace 72 is the corrected output signal ($\hat{S}_A$) after subtraction of the correction value ($\hat{B}_A$) from the uncorrected signal ($S_A$).

In total, nine corrected output signals ($\hat{S}_A$) are generated. These corrected output signals provide a good indication of the content of the speech (hereafter referred to as the "unknown speech") on which the signals are based.

The corrected output signals could, for example, be used to determine the words being spoken. There are a number of ways of doing this. In one such method, the nine corrected output signals are compared to a database of pre-recorded corrected signals that have been generated in an identical manner, by the same individual, with the same magnets 10-20 fixed to the same articulators 22, 24, 26, the same support 28, the same signal and reference sensors 32, 34, 36, 38, and using the same method of generating corrected output signals ($\hat{S}_A$). During the pre-recording, the individual reads out a series of words or phrases ensuring that all phonemes (the sounds from which words are constructed) are fully represented. Comparison of the nine corrected output signals ($\hat{S}_A$) generated from the unknown speech with the pre-recorded database allows the phonemes, and thus the words, in the unknown speech to be identified. The comparison can be performed using any suitable known method. One suitable known method is referred to as Dynamic Time Warping. This method is well known to the skilled person and will not be described in detail here.

Once the words of the unknown speech have been identified, they can be used, for example, to generate artificial speech, for communication, or to operate machinery.

It will be appreciated that many modifications may be made to the embodiment described above while remaining within the scope of the claims.

In the embodiment described above, the reference magnetic field sensor unit 38 is distanced sufficiently far from the magnets 10-20 so that the three magnetic field intensities (in the three axes x, y and z) sensed by the reference magnetic field sensor unit 38 do not include any substantial component from the magnets 10-20. Although this is the preferred arrangement, this need not be the case. Instead, the distance may be such that the contribution from the magnets 10-20 to the three magnetic field intensities (in the three axes x, y and z) sensed by the reference magnetic field sensor unit 38 is significant (but normally less than the contribution from the magnets 10-20 to the nine magnetic field intensities sensed by the three signal magnetic field sensor units 32-36).

When the reference magnetic field sensor unit 38 is able to sense the magnets 10-20, then the mathematics underlying the modified method are set out below.

Equation 1 remains the same but the reference sensor signal now depends on the background (Earth's) field and the magnetic fields of the magnets 10-20:

$$S_R = B_E T_R + AN \quad (6)$$

Where N is a spatial transformation between the magnetic fields of the magnets and the reference sensors.

The new estimate of the background (Earth's) field for the signal sensor can be calculated by substituting equation 6 into equation 3:

$$\hat{B}_A = S_R \hat{T}_{RA} = B_E T_R \hat{T}_{RA} + AN\hat{T}_{RA} \quad (7)$$

The signal sensor signal with background cancellation remains $$\hat{S}_A = S_A - \hat{B}_A \quad (8)$$

Substituting (1) and (7) into (8) gives:

$$\hat{S}_A = A + B_A - S_R \hat{T}_{RA} = A + B_E T_A - B_E T_R \hat{T}_{RA} - AN\hat{T}_{RA}$$

Or, again using the fact that $T_R \hat{T}_{RA} = \hat{T}_A$ $$\hat{S}_A = A(I - N\hat{T}_{RA}) + B_E(T_A - \hat{T}_A) \quad (9)$$

And if $\hat{T}_A$ provides a good estimate of $T_A$ then $$\hat{S}_A = A(I - NT_{RA}) \quad (10)$$

The $ANT_{RA}$ term is the part of speech information cancelled from the signal sensor when the reference sensor is close to the magnets and so picks up speech information.

Provided the matrix $(I-NT_{RA})$ is non-singular then the signal sensor signal can be extracted from $\hat{S}_A$.

In the embodiment discussed above, magnets 10-20 are fixed to the tongue 22 and to the lips 24, 26. However, the magnets may be fixed to any suitable articulators. Preferably, each magnet is attached to a respective articulator that moves during speech so that the magnetic field intensity sensed by any one of the signal magnetic field sensors and attributable to that magnet changes as the individual talks or mouths speech. The articulators, including the articulators that move during speech are well known to the skilled person. A suitable articulator may be chosen for attachment of a magnet both with a view to producing a magnetic field which undergoes significant change during speech but also to minimise discomfort to the individual. The number of magnets may also be varied.

The number of signal magnetic field sensors may be varied. It has been found that the use of nine signal magnetic field sensors provides a good result. Using fewer signal sensors is possible but it becomes harder to resolve phonemes. Using more than nine signal sensors provides excellent resolution of phonemes but requires greater processing capacity. It is not essential to provide the magnetic field sensors in the form of sensor units 32-38 which contain three sensors arranged to detect magnetic field intensity in three mutually orthogonal directions. Individual uniaxial sensors may be used.

The support may be of any suitable configuration.

The invention claimed is:

1. A method of producing output indicative of the content of speech or mouthed speech from movement of speech articulators, comprising:
    fixing a plurality of magnets respectively to a plurality of speech articulators of a human individual;
    providing a support;
    providing a plurality of signal magnetic field sensors, each said signal magnetic field sensor being located so as to be able to sense a respective magnetic field intensity comprising a component produced by at least one of the magnets and a component produced by the Earth's magnetic field;
    providing at least three reference magnetic field sensors orientated differently from one another with respect to the Earth's magnetic field, each said reference magnetic field sensor being located so as to be able to sense a respective magnetic field intensity produced at least partially by the Earth's magnetic field;
    the signal and reference magnetic field sensors being fixed to the support which holds the sensors in fixed spatial relationships to one another;
    producing, over a period of time, a respective signal from each signal magnetic field sensor and a respective signal from each reference magnetic field sensor, each signal being indicative of a respective magnetic field intensity sensed by the corresponding magnetic field sensor, wherein over said period of time the signals from the signal and reference magnetic field sensors change in response to movement of the support relative to the Earth's magnetic field, and the signals from the signal magnetic field sensors, and optionally also the signals from the reference magnetic field sensors, change in response to movement of the articulators; and
    obtaining, over said period of time, for each said signal magnetic field sensor signal, a respective correction value, each correction value being indicative of the component that is produced by the Earth's magnetic field in the magnetic field intensity sensed by the corresponding signal magnetic field sensor and each correction value changing over said time period as the component that is produced by the Earth's magnetic field in the magnetic field intensity sensed by the corresponding signal magnetic field sensor changes as the support moves;
    wherein each correction value is calculated using the signals from the at least three reference magnetic field sensors, and also using a respective spatial transformation, each spatial transformation relating the orientations of each of said at least three reference magnetic field sensors to the orientation of the corresponding signal magnetic field sensor.

2. The method as claimed in claim 1, and further including estimating said spatial transformations.

3. The method as claimed in claim 2, wherein each said spatial transformation is estimated using a least squares method using the signals from the at least three reference magnetic field sensors and the signal from the signal magnetic field sensor to which the transformation relates, said signals which are used for said estimation being obtained as the support is moved such that the changes in magnetic field intensities sensed by the magnetic field sensors are attributable substantially only to movement of the magnetic field sensors relative to the Earth's magnetic field.

4. The method according to claim 1, further including using the correction values to correct the signals from the signal magnetic field sensors produced over said period of time to give corrected output signals in which variation is predominantly caused by movement of the articulators.

5. The method according to claim 4, wherein the corrected output signals are used to identify the content of speech or mouthed speech made by the individual during said period of time.

6. The method according to claim 5, further including using said identified content of speech or mouthed speech to generate artificial speech corresponding to the speech or mouthed speech made by the individual during the period of time.

7. The method according to claim 1, wherein the support is worn on the head of the human individual over said period of time, the support moving with the head of the human individual when the support is so worn.

8. The method according to claim 1, wherein, over said period of time, the distance from each reference magnetic field sensor to the one of the magnets which is closest to the reference magnetic field sensor is greater than the respective distance from each signal magnetic field sensor to the respective one of the magnets which is closest to said each signal magnetic field sensor, whereby the respective magnetic field intensity sensed by each reference magnetic field sensor either includes substantially no component produced by the magnets or includes a component produced by the magnets which is lower in magnitude than each respective magnetic field component produced by the magnets and sensed by each of the signal magnetic field sensors.

9. The method according to claim 1, wherein there are three reference magnetic field sensors and wherein the three reference magnetic field sensors sense magnetic field intensity in three mutually orthogonal axes, respectively.

10. The method according to claim 9, wherein the three reference magnetic field sensors are comprised within a tri-axial reference sensor unit.

11. The method according to claim 1, wherein, over said period of time, each said reference magnetic field sensor is sufficiently far from the magnets so that the magnetic field intensity sensed by the reference magnetic field sensor includes substantially no component from the magnets.

12. The system for performing the method of claim 1, comprising:
a plurality of magnets fixable respectively to a plurality of speech articulators of a human individual;
a plurality of signal magnetic field sensors for sensing respective magnetic field intensities;
at least three reference magnetic field sensors for sensing respective magnetic field intensities;
a support to which the signal and reference magnetic field sensors are fixed and which holds the sensors in fixed spatial relationships to one another.

13. The system according to claim 12, wherein the support is adapted to be worn on a head of a human.

14. The system according to claim 12, wherein there are three reference magnetic field sensors and wherein the three reference magnetic field sensors are comprised within a tri-axial reference sensor unit.

15. A system for performing the method of claim 3, comprising:
a plurality of magnets fixable respectively to a plurality of speech articulators of a human individual;
a plurality of signal magnetic field sensors for sensing respective magnetic field intensities;
at least three reference magnetic field sensors for sensing respective magnetic field intensities;
a support to which the signal and reference magnetic field sensors are fixed and which holds the sensors in fixed spatial relationships to one another.

16. The system according to claim 15, wherein the support is adapted to be worn on a head of a human.

17. The system according to claim 15, wherein there are three reference magnetic field sensors and wherein the three reference magnetic field sensors are comprised within a tri-axial reference sensor unit.

18. A system for performing the method of claim 4, comprising:
a plurality of magnets fixable respectively to a plurality of speech articulators of a human individual;
a plurality of signal magnetic field sensors for sensing respective magnetic field intensities;
at least three reference magnetic field sensors for sensing respective magnetic field intensities;
a support to which the signal and reference magnetic field sensors are fixed and which holds the sensors in fixed spatial relationships to one another.

* * * * *